United States Patent [19]
Van Iderstine

[11] Patent Number: 6,164,275
[45] Date of Patent: Dec. 26, 2000

[54] INHALER CARRIER

[76] Inventor: Lois Van Iderstine, 120 Riva Blvd., Brick, N.J. 08723

[21] Appl. No.: 09/232,260

[22] Filed: Jan. 19, 1999

[51] Int. Cl.[7] .................................................. A61M 11/00
[52] U.S. Cl. .............................. 128/200.14; 128/200.21; 128/200.23; 128/203.15; 128/203.12; 128/205.22
[58] Field of Search ........................ 128/200.14, 200.23, 128/203.12, 203.15, 200.21, 203.23, 912, 205.24, 205.22, 200.18; 222/94; 239/507; 604/58

[56] References Cited

U.S. PATENT DOCUMENTS

| | | | |
|---|---|---|---|
| 4,114,811 | 9/1978 | Loeffler | 239/288 |
| 5,243,972 | 9/1993 | Huang | 128/205.22 |
| 5,582,164 | 12/1996 | Sanders | 128/205.22 |
| 5,730,118 | 3/1998 | Hermanson | 128/200.14 |
| 5,769,073 | 6/1998 | Eason et al. | 128/203.15 |
| 5,855,307 | 1/1999 | Biddick et al. | 224/267 |
| 5,860,416 | 1/1999 | Howlett | 128/200.23 |
| 5,865,175 | 2/1999 | Chu | 128/205.22 |
| 5,899,200 | 5/1999 | McNary | 128/200.14 |

*Primary Examiner*—John G. Weiss
*Assistant Examiner*—V. Srivastava
*Attorney, Agent, or Firm*—Louis S. Gillow

[57] ABSTRACT

An inhaler carrier holds a plastic actuator enclosing a medical cannister, which inhaler carrier is comprised of three oval loops: the first loop of which supports the upper portion of the plastic actuator having a barrel shape at its upper portion for inserting the medical cannister; the second loop of which contains and supports the lower portion of the plastic actuator; and the third loop of which is affixed to the first and second loops in order to support and carry the medical cannister within the plastic actuator for use by the user transporting the inhaler carrier. The plastic actuator includes a hinged or removable cap which protects and encloses an aerosol chamber with a mechanism for atomizing the material in the medical cannister into the nose or mouth of the user.

2 Claims, 1 Drawing Sheet

INHALER CARRIER

This invention relates to an inhaler carrier for transporting a medical cannister containing an oral or nasal medication within a plastic actuator. The inhaler carrier is securely attachable to a person who can easily open and actuate the medical cannister when it is necessary.

BACKGROUND OF THE INVENTION

Persons with pulmonary or upper respiratory associated diseases often use nasal or oral aerosol sprays in order to control their diseases. Generally, nasal or oral sprays are atomized medications contained in a medical cannister having a plastic aerosol tube or nozzle. The medical cannister of the present invention is the Albuterol U.S. Aerosol 17 g, 200 metered inhalation supplied by Warrick Pharmaceuticals Corporation, Niles, Ill. 60714. Plastic actuators are usually provided by the medical cannister manufacturer to receive and contain the medical cannister and to seat the nozzle. The plastic actuator for the present invention is Allen & Hanburys Ventolin® (Albuterol, U.S.P.) Inhalation Aerosol, also supplied by Warrick Pharmaceuticals, Niles, Ill. 60714. The nozzle is typically actuated by applying downward pressure on the medical cannister within the plastic actuator. The nozzle is deformed when pressed so as to release and atomize the medication within the medical cannister into an aerosol chamber within the plastic actuator. The aerosol chamber of the plastic actuator is inserted or pressed against the nose or mouth of the user for inhalation of the medication within the medical cannister for control of the pulmonary or upper respiratory associated disease.

Persons with asthma or other seven pulmonary or upper respiratory associated diseases must often resort to aerosol medications for acute life-threatening attacks. Therefore, it is essential that the medical cannister cylinder and plastic actuator be assembled at-the-ready for immediate use. This requires the medical cannister and the plastic actuator to be assembled and immediately useable by the person requiring the aerosol medication.

It is an object of the present invention to safely carry the assembled medical cannister and plastic actuator by the person needing the treatment.

It is another object of the present invention to protect the asembled medical cannister and plastic actuator within the inhaler carrier so as to maintain its integrity and cleanliness.

It is a further object of the present invention to secure the inhaler carrier onto the person transporting the assembled medical cannister and plastic actuator within the inhaler carrier.

These and other objects of the present invention will become more apparent upon considering the following description of the present invention taken in conjunction with the drawing.

BRIEF DESCRIPTION OF THE DRAWINGS

One preferred embodiment of the present invention is hereafter described with refence to the following drawings, in which.

DETAILED DESCRIPTION

Figure 1:
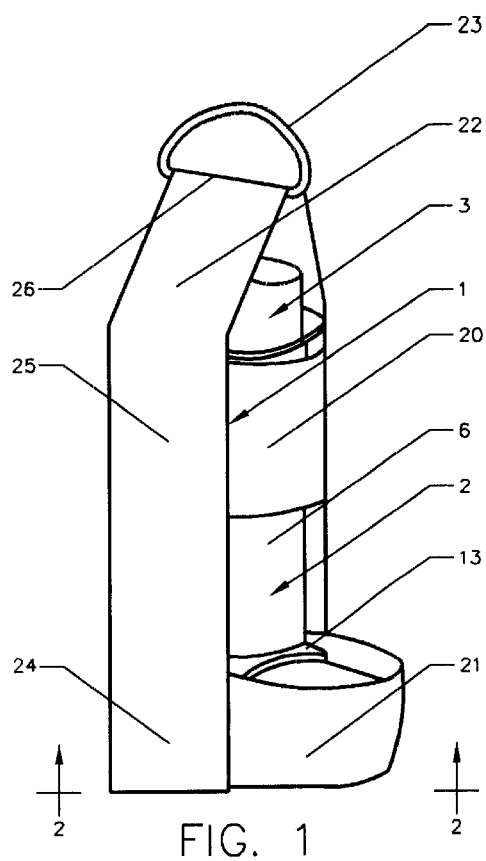
FIG. 1 is perspective view of the inhaler carrier of the present invention, and therein the medical cannister contained within the plastic actuator.

Referring now to FIG. 1 there is shown a perspective viewed from the side and slightly above the inhaler carrier, generally referred to as 1, of the present invention. Contained within the inhaler carrier 1 is a plastic actuator, generally referred to as 2. A medical cannister in the form of a metal cylinder 3 contains a medication for aerosol inhalation orally or nasally. The medical cannister 3 is placed downward within the barrel-shaped upper portion 6 of the plastic actuator 2. The upper portion 6 of the plastic actuator 2 is encircled and contained by a first piece of material 20 made of a continuous webbed strap in the form of an oval loop. The lower portion 13 of the plastic actuator 2 is encircled and contained by a second piece of material 21 made of a continuous knit elastic tape in the form of an oval loop spaced parallel and below the first piece of material 20. The first piece of material 20 and the second piece of material 21 are affixed perpendicularly to the interior of a third piece of material 22 made of a continuous webbed strap in the form of an oval loop. The bottom portion 24 of the third piece of material 22 is attached perpendicularly and externally along each side of the second piece of material 21 which encircles and supports the lower portion 13 of the plastic actuator 2. The middle portion 25 of the third piece of material 21 is attached perpendicularly and externally along each side of the first piece of material 20 encircling and containing the upper portion 6 of the plastic actuator 2. The top portion 26 of the third piece of material 21 encloses a metal D-ring 23 which is used to attach the inhaler carrier 1 to a desired location on the person transporting the inhaler carrier 1. The attachment of the D-ring 23 to the person may be accomplished by attachment means, such as, but not limited to, a chain, a ring, a clip, a safety pin, etc. attaching the inhaler carrier 1 to the user.

Figure 2:
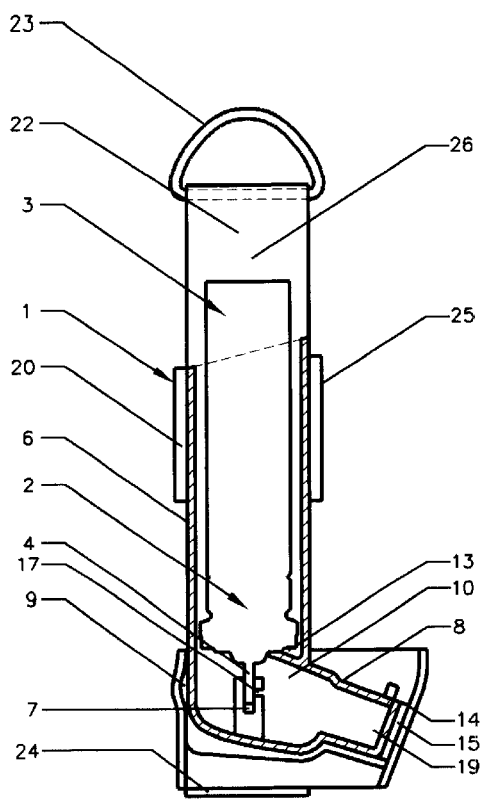
FIG. 2 is a side sectional view taken along line 2-2' of FIG. 1.
Figure 3:
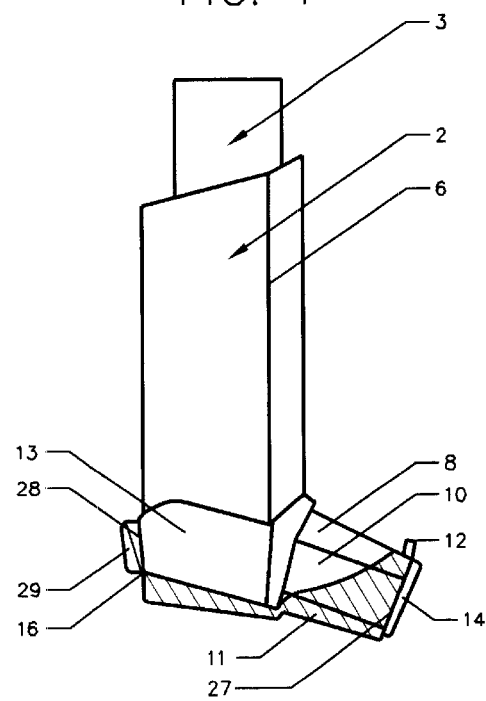
FIG. 3 is a side view of the medical cannister contained within the plastic actuator.
Figure 4:
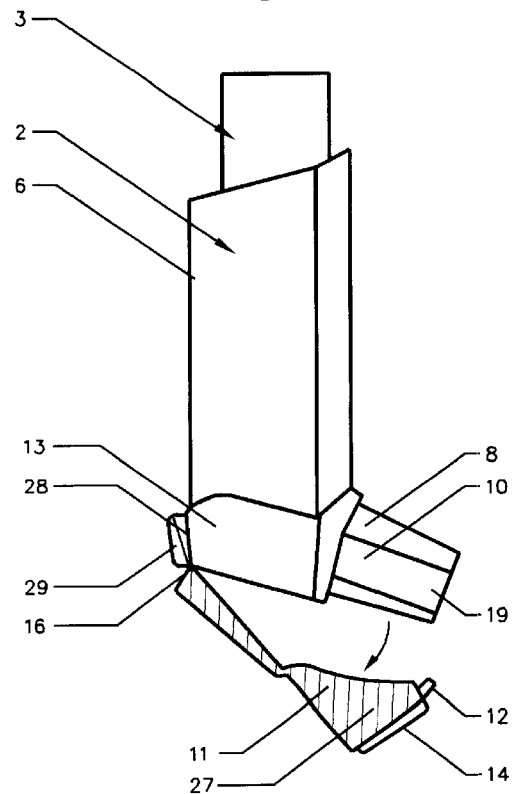
FIG. 4 is a side view of the medical cannister contained within the plastic actuator shown in FIG. 3 with the cap snapped downward from the plastic actuator before actuation of an aerosol from the medical cannister.

Referring now to FIG. 2 there is shown a side sectional view of the inhaler carrier 1 along line 2-2' of FIG. 1. The inhaler carrier 1 has the first piece of material 20 encircling and supporting the upper portion 6 of the plastic actuator 2 which is in the form of a barrel opening upward. Into the upper portion barrel 6 a medical cannister 3 is placed with its aerosol nozzle tube 4 downward into the barrel 6 and seated into the aerosol channel 7 in the lower portion 13 of the plastic actuator 2. The aerosol nozzle tube 4 seated within the aerosol channel 7 is deformed by the user placing downward finger pressure on the medical cannister 3 so that it slides downward within the barrel of the upper portion portion 6 of the plastic actuator 2. The deformation of the aerosol nozzle tube 4 within the aerosol channel 7 causes the medicine in the medical cannister 3 to be released and atomized through the channel opening 17 into the aerosol chamber 10 at the lower portion 13 of the plastic actuator 2. The aerosol chamber 10 has an outward opening 19 from the plastic actuator 2. As shown in FIGS. 2, 3 and 4 the outward opening 19 is normally closed by a plastic cap 11, the cover 27 of which is placed over the outward opening 19. The cap 11 is affixed at its opposite end 28 from the outward opening 19 by a cap tab 29 adhered to a projection 9 on the lower portion 13 of the plastic enclosure 2. The cap cover 27 has a cover tab 12 which facilitates finger grasping of the cover 27 and swinging movement downward by the user along the hinge 16 of the cap 11. After opening the cap 11 the user places the outward opening 19 of the aerosol chamber 10 over either his nose or mouth. The user then moved the medical cannister 3 downward by finger pressure within the plastic actuator 2 so as to release and atomize the contents of the medical cannister 3 into the aerosol chamber 10 and thence to the user's nose or mouth.

Referring now to FIGS. 3 and 4 there is shown a side view of the plasic actuator 2 with the medical cannister 3 inserted within the plastic actuator 2. FIG 3 shows the plastic actuator 2 with the cover 27 of the plastic cap 11 closing the outward opening 19 of the aerosol chamber 10 in the lower portion 13 of the plastic actuator 2. FIG. 4 shows the cover 27 of the plastic cap 11 swung downward by finger pressure of the user from the aerosol chamber 10 of the lower portion 13 of the plastic actuator 2. This downward movement of the cover 27 of the plastic cap 11 opens the aerosol chamber 8 to deliver the atomized contents of the medical cannister as an aerosol into the nose or mouth of the user.

An alternative embodiment of the present invention is also shown in FIGS. 2, 3 and 4. A hook closure disc 14 is adhered to the exterior periphery of the cover 27 of the cap 11. A loop closure disc 15 is adhered to the interior of the second piece of material 21 in mating engagement with the hook closure disc 14 on the cover 27. When the plastic actuater 2 and medical cannister 3 are contained within the inhaler carrier 1, the hook closure disc 14 and the loop closure disc 15 releasably lock into place to more securely hold the assembled plastic actuator 2 and medical cannister 3 within the inhaler carrier 1. When it is required to actuate an aerosol from the medical cannister 3, the user moves the second piece of material 21 away from the cover 27 of the cap 11 releases or unlocks the hook closure 14 from the loop closure 15 by easy finger pressure so that the cover 27 of the cap 11 can be swung downward to expose the nose or mouth of the user to the outward opening 19 of the aerosol chamber 10 for treatment. Hook and loop closure discs are available is VELCRO® Disc Closures from the Velcro Corporation New York, N.Y.

It should be noted that there are variations of the medical cannister 3 available from different manufacturers of inhalation aerosols. Therefore it may be necessary to provide different sized or shaped plastic actuators 2 in order to accept such variations of medical cannisters 3 within the inhaler carrier 1 of the present invention. It is also apparent to those skilled in the art that a plastic actuator 2 can be supplied with a detachable cap 11 over the aerosol chamber 10. Although workable, that embodiment is not considered as secure as the preferred embodiment of the present invention.

The foregoing description of the present invention is for the purpose of illustration, and is not limiting to the scope of the present invention which is set forth in the appended claims:

What is claimed is:

1. An inhaler carrier adapted for use with a standard oral or nasal inhalation assembly, consisting of a cylindrical medical cannister inserted downward within a plastic actuator enclosure having an open barrel shape at its upper portion, said plastic actuator enclosure having at its lower portion an aerosol chamber opening outwardly from the plastic actuator enclosure, said aerosol chamber being normally covered by a cap when not in use, whereby the inhaler carrier comprises:

a first piece of material in the form of a continuous webbed strap affixed in an oval loop adapted to encircle and support said barrel of said plastic actuator enclosure;

a second piece of material in the form of a continuous knit elastic tape affixed in an oval loop parallel and spaced below said first piece of material, said tape loop adapted to encircle and support said lower portion of said plastic actuator enclosure and said cap of said aerosol chamber;

a third piece of material in the form of a continuous webbed strap oval loop having a bottom portion of said loop affixed perpendicularly along opposite exterior sides of said second piece of material and adapted to encircle and support said lower portion of said plastic actuator and said cap of said aerosol chamber, a middle portion of said loop of the third piece of material being spaced parallel and above said bottom portion and affixed perpendicularly along opposite exterior sides of said first piece of material adapted to encircle and support said barrel; and a metal D-ring enclosed within a top portion of said loop of the third piece of material, whereby attachment means are connected to said D-ring to aid in attaching said inhaler carrier to any desired location on the person carrying the inhaler carrier.

2. The inhaler carrier according to claim 1 wherein said metal D-ring attachment means include a chain, a ring, a clip or a safety pin connected to said D-ring.

* * * * *